United States Patent
O'Heeron et al.

(10) Patent No.: US 6,544,277 B1
(45) Date of Patent: *Apr. 8, 2003

(54) OBTURATOR ASSEMBLY

(75) Inventors: Peter T. O'Heeron, Houston, TX (US); Lawrence W. Moser, Webster, TX (US); Richard C. Fortier, Concord, MA (US); Terry L. Bohannon, Houston, TX (US)

(73) Assignee: NeoSurg Technologies, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/517,774

(22) Filed: Mar. 3, 2000

Related U.S. Application Data

(63) Continuation-in-part of application No. 09/060,640, filed on Apr. 15, 1998, now Pat. No. 6,106,539.
(51) Int. Cl.⁷ .............................................. A61B 17/34
(52) U.S. Cl. ...................................... 606/185; 606/167
(58) Field of Search ................................ 606/185, 166, 606/167, 168, 169, 170, 171, 180, 183, 186

(56) References Cited

U.S. PATENT DOCUMENTS

| | | | |
|---|---|---|---|
| 649,493 A | | 5/1900 | Stohlmann et al. |
| 756,213 A | * | 4/1904 | Connell, Sr. .................. 606/80 |
| 3,187,431 A | | 6/1965 | Mattes ......................... 30/339 |
| 4,254,762 A | | 3/1981 | Yoon et al. ..................... 128/4 |
| 4,535,773 A | | 8/1985 | Yoon et al. .................... 604/51 |
| 4,601,710 A | | 7/1986 | Moll et al. .................. 604/165 |
| 4,654,030 A | | 3/1987 | Moll et al. .................. 604/165 |
| 4,902,280 A | | 2/1990 | Lander ........................ 604/165 |
| 4,911,575 A | | 3/1990 | Tidwell ........................ 404/97 |
| 4,931,042 A | | 6/1990 | Holmes et al. .............. 604/164 |

(List continued on next page.)

FOREIGN PATENT DOCUMENTS

EP          078 358 A2      1/1982    ............ B25G/3/18

*Primary Examiner*—Michael J. Milano
*Assistant Examiner*—Jessica R Baxter
(74) *Attorney, Agent, or Firm*—Jackson Walker; Clarence E. Eriksen; Bryan P. Galloway

(57) ABSTRACT

An obturator assembly having a removable obturator tip, a first engagement device, an obturator shaft, a second engagement device, and a biased flexible member, whereby the obturator tip may be removed by flexing the flexible member against its bias, and a plurality of different obturator tips may be attached to the obturator shaft.

32 Claims, 9 Drawing Sheets

U.S. PATENT DOCUMENTS

| | | | |
|---|---|---|---|
| 4,985,035 A | 1/1991 | Torre | 606/167 |
| 5,030,206 A | 7/1991 | Lander | 604/164 |
| 5,104,382 A | 4/1992 | Brinkerhoff et al. | 604/165 |
| 5,114,407 A | 5/1992 | Burbank | 604/164 |
| 5,116,353 A | 5/1992 | Green | 606/184 |
| 5,256,147 A | 10/1993 | Vidal et al. | 604/158 |
| 5,256,149 A | 10/1993 | Banik et al. | 604/164 |
| 5,275,583 A | 1/1994 | Crainich | 604/264 |
| 5,312,354 A | 5/1994 | Allen et al. | 604/157 |
| 5,330,493 A | 7/1994 | Haining | 606/167 |
| 5,342,379 A | 8/1994 | Volinsky | 606/167 |
| 5,350,393 A | 9/1994 | Yoon | 606/185 |
| 5,364,372 A | 11/1994 | Danks et al. | 604/264 |
| 5,387,197 A | 2/1995 | Smith et al. | 604/167 |
| 5,405,328 A | 4/1995 | Vidal et al. | 604/158 |
| 5,411,515 A | 5/1995 | Haber et al. | 606/184 |
| 5,431,635 A | 7/1995 | Yoon | 604/165 |
| 5,486,190 A | 1/1996 | Green | 606/184 |
| 5,507,774 A | 4/1996 | Holmes et al. | 606/208 |
| 5,522,833 A | 6/1996 | Stephens | 606/185 |
| 5,538,509 A | 7/1996 | Dunlap et al. | 604/264 |
| 5,549,564 A | 8/1996 | Yoon | 604/165 |
| 5,551,947 A | 9/1996 | Kaali | 604/264 |
| 5,554,137 A | 9/1996 | Young et al. | 604/264 |
| 5,554,167 A | 9/1996 | Young et al. | 606/184 |
| 5,569,285 A * | 10/1996 | Webb | 606/180 |
| 5,569,289 A | 10/1996 | Yoon | 606/185 |
| 5,591,190 A | 1/1997 | Yoon et al. | 606/185 |
| 5,607,440 A | 3/1997 | Danks et al. | 606/185 |
| 5,609,604 A | 3/1997 | Schwemberger et al. | 606/185 |
| 5,645,076 A | 7/1997 | Yoon | 128/754 |
| 5,645,556 A | 7/1997 | Yoon | 606/185 |
| 5,664,792 A | 9/1997 | Tseng | 403/325 |
| 5,669,885 A | 9/1997 | Smith | 606/184 |
| 5,674,184 A | 10/1997 | Hassler | 600/176 |
| 5,674,237 A | 10/1997 | Ott | 606/185 |
| 5,676,681 A | 10/1997 | Yoon | 606/185 |
| 5,676,682 A | 10/1997 | Yoon | 606/185 |
| 5,678,683 A | 10/1997 | Yoon | 606/195 |
| 5,685,820 A | 11/1997 | Riek et al. | 600/114 |
| 5,688,286 A | 11/1997 | Yoon | 606/185 |
| 5,697,947 A | 12/1997 | Wolf et al. | 606/185 |
| 5,720,761 A | 2/1998 | Kaali | 606/185 |
| 5,797,944 A | 8/1998 | Nobles et al. | 606/185 |
| 5,810,863 A | 9/1998 | Wolf et al. | 606/185 |
| 5,842,387 A * | 12/1998 | Marcus et al. | 606/180 |
| 5,868,773 A | 2/1999 | Danks et al. | 606/185 |
| 6,106,539 A * | 8/2000 | Fortier | 606/185 |

* cited by examiner

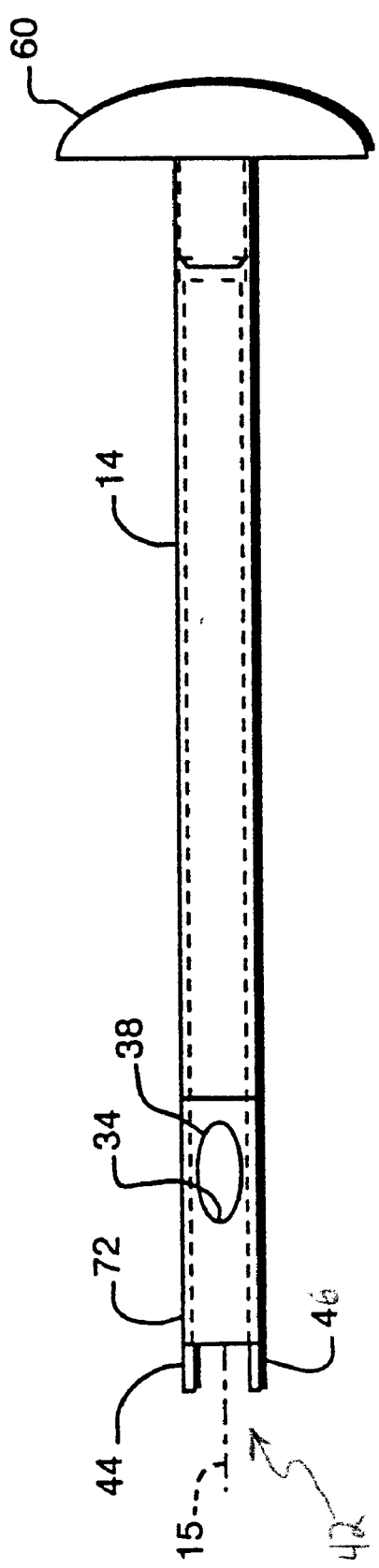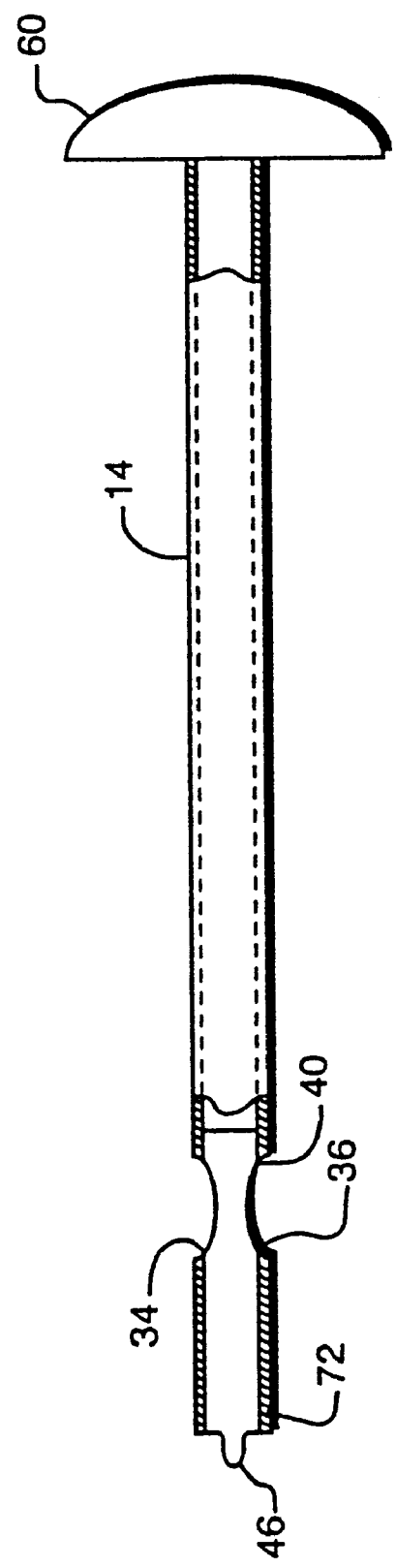
FIG. 3
FIG. 4

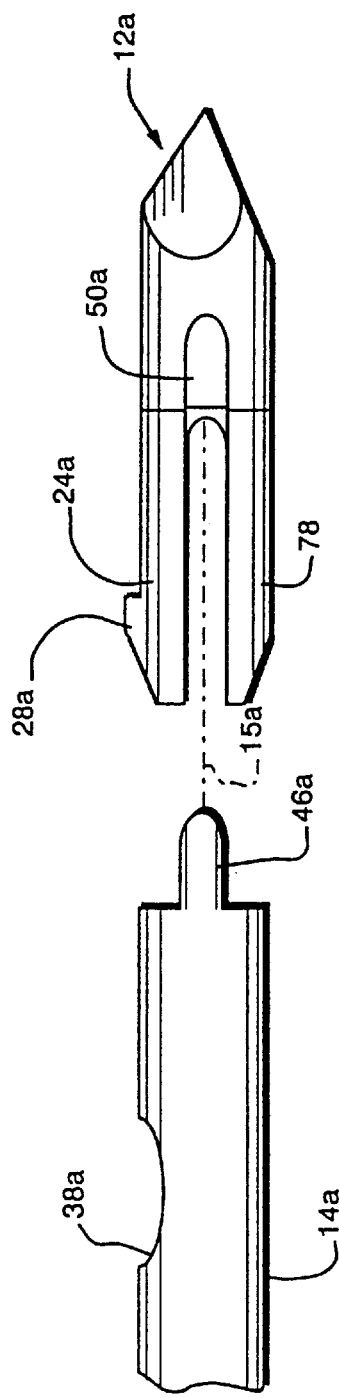
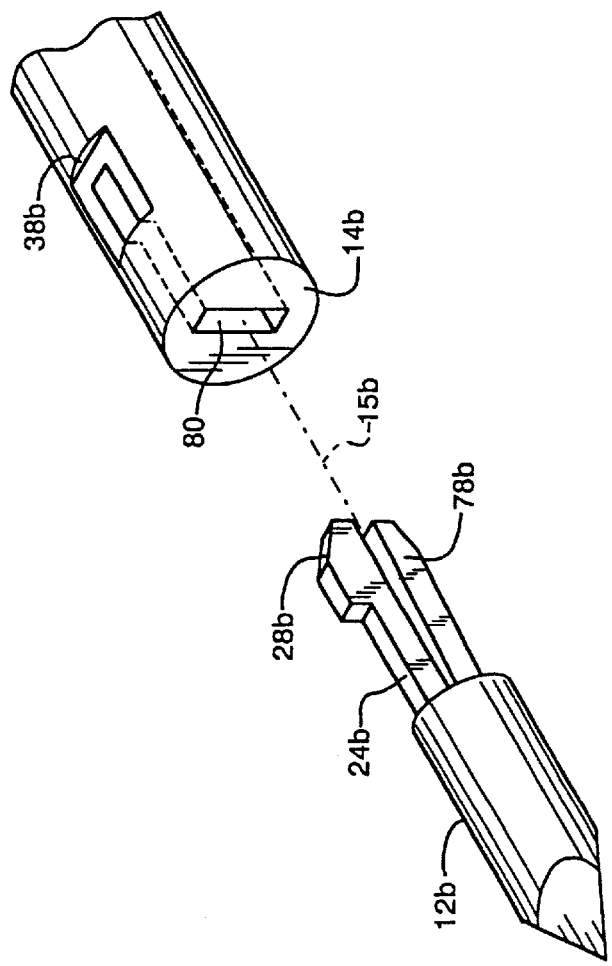
FIG. 5
FIG. 6

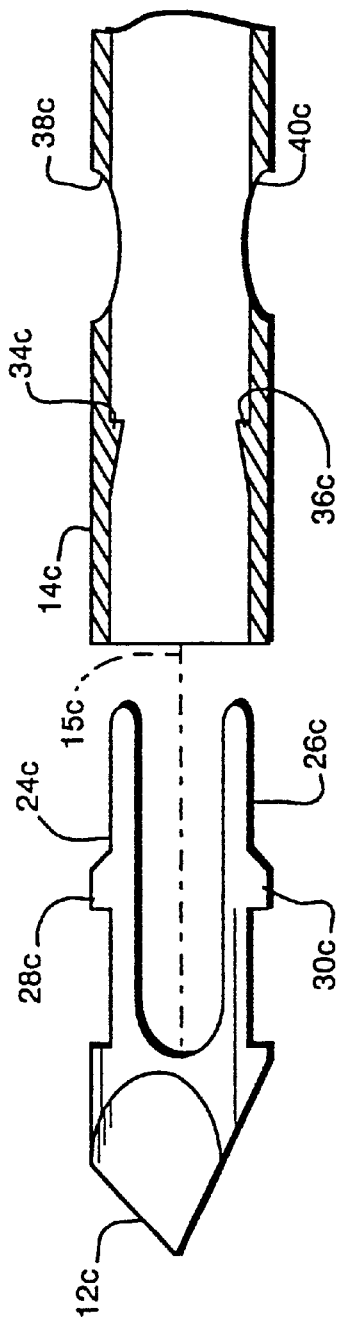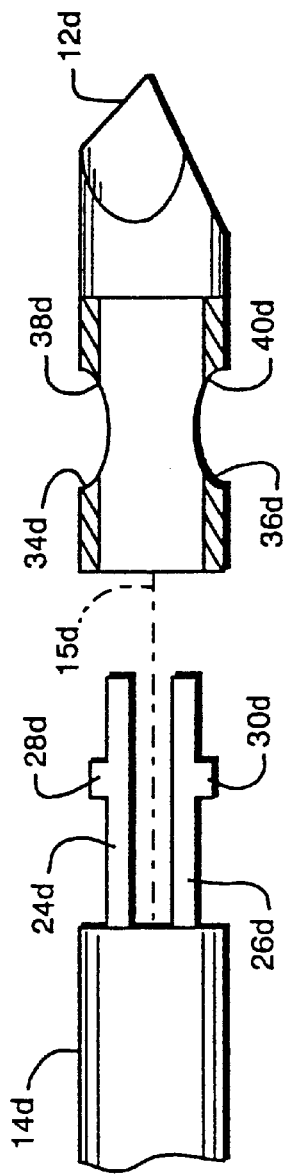

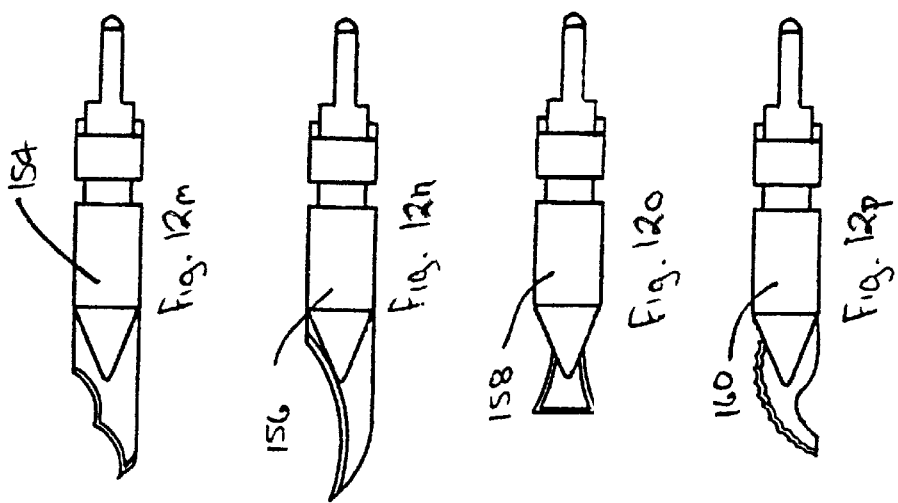
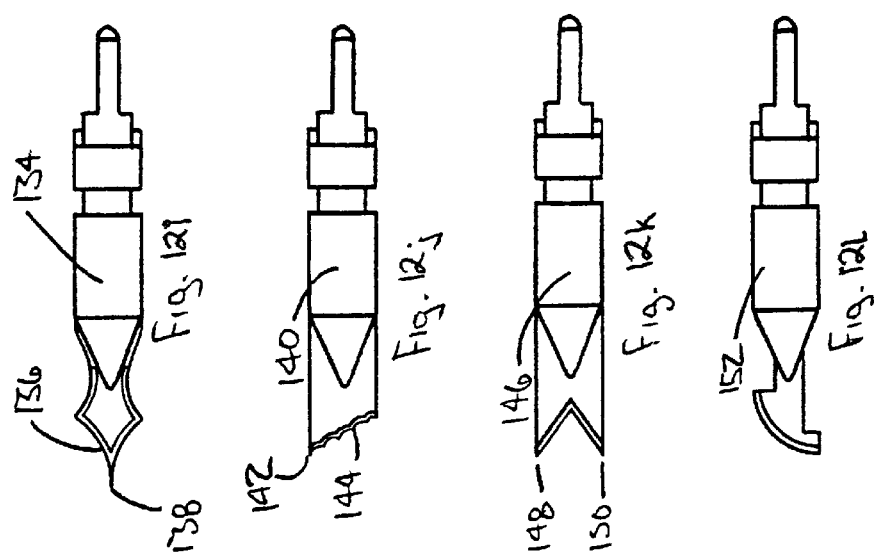
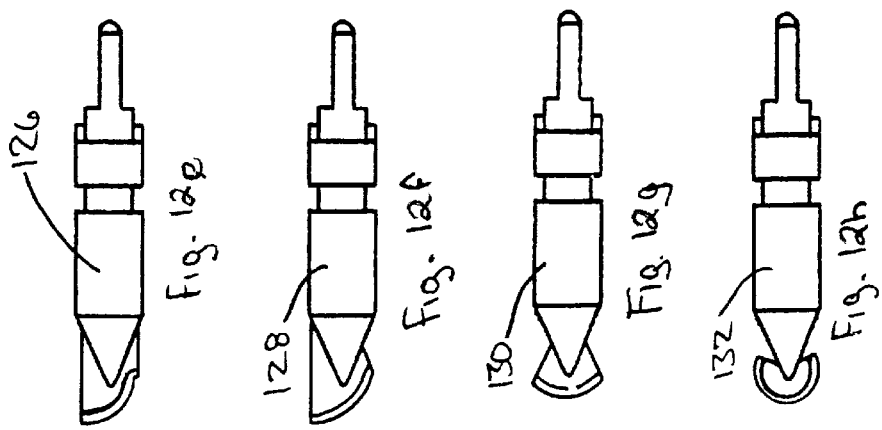

OBTURATOR ASSEMBLY

CROSS REFERENCE TO RELATED APPLICATIONS

This application is a continuation-in-part of U.S. Ser. No. 09/060,640, now U.S. Pat. No. 6,106,539 filed Apr. 15, 1998.

BACKGROUND OF THE INVENTION

1. Field of Invention

This invention relates to an obturator having a removable, replaceable tip and more particularly to such a removable, replaceable tip that flexibly engages and releases the obturator tip from the shaft.

2. Description of the Prior Art

Conventional trocars use an obturator with a sharp metal tip to penetrate a body cavity in surgical procedures. After each use, the obturator must be sterilized and eventually the tip dulls and must be re-sharpened by machining. These obturators are expensive and adding to their effective cost is the cost of sharpening, sterilizing and the loss of use during those procedures. Some trocars are made to be disposable, i.e., they are used once and discarded with no need for resharpening or sterilizing. Their initial cost is, however, quite high. Alternatively, some trocar obturators are made with a removable metal tip. During the course of surgery, these obturators will often have to be changed to conform to the particular demands of that surgical procedure. However, these tips are also expensive and must be regularly sterilized and periodically re-sharpened. Moreover, obturator shafts tend to be sold without a cutting tip. The tips are sold individually, which requires the surgeon or hospital to maintain a complex and diverse inventory.

SUMMARY OF THE INVENTION

The obturator assembly of the present invention may comprise: a removable obturator tip having a sharpened distal end and a proximal end; a first engagement device disposed on the proximal end of the removable obturator tip; an obturator shaft having a distal end; a second engagement device disposed on the distal end of the obturator shaft adapted to lockingly engage the first engagement device, thereby securing the removable obturator tip to the obturator shaft; and a biased flexible member adapted to flexibly engage the first engagement device to the second engagement device, the flexible member being accessible whereby the flexible member can be flexed against its bias to disengage the first engagement device from the second engagement device.

In specific embodiments of the present invention, the sharpened distal end of the obturator tip: (a) may have a serrated cutting edge; (b) may have a piercing cutting edge; (c) may have a blunt cutting edge; (d) may have a radial cutting edge; (e) may have a cutting edge that cuts and dilates in two directions; (f) may make an incision that is linear and easy to close; (g) may have a semi-circular cutting edge; (i) may have a double beveled cutting edge; (j) may have a claw shaped cutting edge; (k) may create an incision that allows the obturator tip to be rotated as the incision is made; (l) may have a triangular cutting edge; (m) may have a hooked blade cutting edge; (n) may have a sickle shaped cutting edge; (o) may have a flat cutting edge.

The obturator assembly of the present invention may also comprise: a removable obturator tip having a sharpened distal end and a proximal end; a biased flexible leg extending from the proximal end of the tip, the flexible leg having a detent; an obturator shaft having a stop, the stop being adapted to engage the detent on the biased flexible leg, thereby connecting the tip to the obturator shaft; and an access port disposed on the obturator shaft, whereby the flexible leg can be moved against its bias to disengage the detent from the stop.

BRIEF DESCRIPTION OF THE DRAWINGS

In the accompanying drawings:

FIG. 2A is a cross-sectional view taken along lines 2A—2A of FIG. 2 showing a groove that has a circular shape;

FIG. 2B is a view similar to FIG. 2A in which the groove has a polygonal shape;

FIG. 2C is a view similar to FIGS. 2A and 2B wherein the groove has a square shape;

FIG. 3 is an enlarged detailed plan view of the obturator shaft of FIG. 1;

FIG. 4 is an enlarged detailed elevational view of the obturator shaft of FIG. 1;

FIG. 5 is a view similar to FIG. 2 wherein there is but one flexible leg, one detent and one access hole;

FIG. 6 is a three-dimensional view of the tip of FIG. 5 showing an asymmetric slot in the shaft for definitively orienting the tip and shaft assembly;

FIG. 7 is an enlarged detailed side elevational view of another embodiment of the removable replaceable tip according to this invention employing two flexible legs with detents for mating with internal stop shoulders on the shaft;

FIG. 8 is a view similar to FIG. 7 of another embodiment of the removable replaceable tip according to this invention in which flexible legs with detents are on the shaft and the tip contains access ports a portion of which function as stop recesses;

DESCRIPTION OF THE PREFERRED EMBODIMENTS

Figure 1:
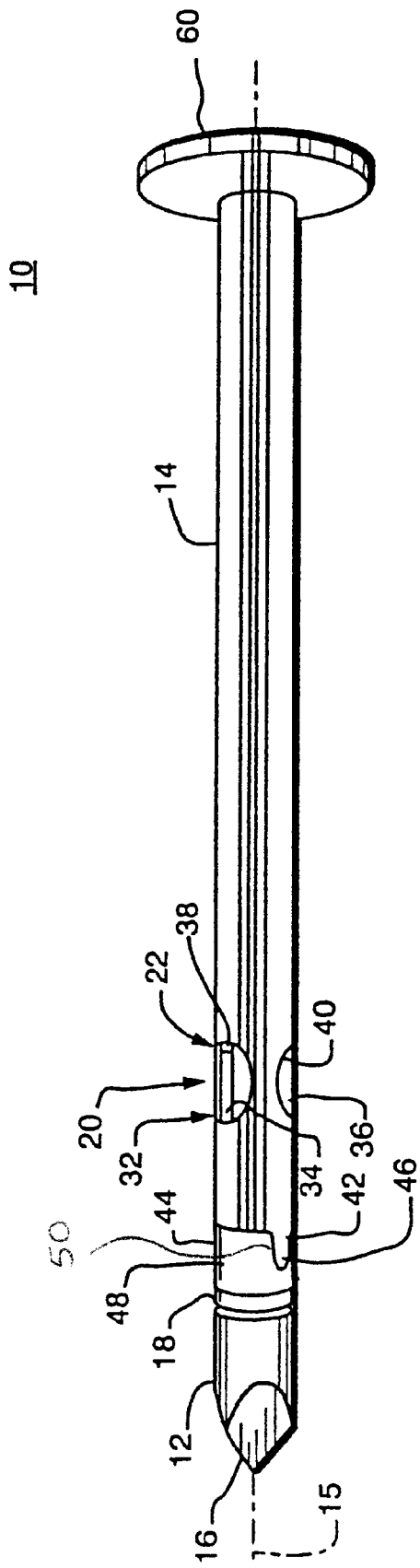
FIG. 1 is a three-dimensional view of an obturator assembly including a removable replaceable tip according to this invention.

FIG. 1 shows an obturator assembly 10 according to this invention. The obturator assembly 10 may preferably include an obturator tip 12 and shaft 14 with a longitudinal axis 15. Tip 12 may include a sharpened distal end 16 and a removal groove 18 for receiving, for example, forceps, to remove tip 12 from shaft 14. Referring to FIGS. 1, 2, 3 and 4, it can be seen that there are engagement means 20 which generally include an engagement device 22 on tip 12 which may be comprised of a pair of flexible legs 24, 26 having detents 28 and 30. There may also an engagement device 32 on shaft 14 which may include the stop means formed by the stop recesses 34 and 36 that can form a part of the oval ports 38 and 40 that preferably constitute the access means by which the fingers of a surgeon can reach and squeeze legs 24 and 26 to move detents 28 and 30 out of contact with stop recesses 34 and 36 in order to release tip 12 from shaft 14. Flexible legs 24 and 26 preferably have a sufficient bias to maintain detents 28 and 30 in contact with stop recesses 34 and 36. The bias of flexible legs 24 and 26 is preferably sufficient to provide a snap fit. This snap fit may cause there to be a clicking noise when tip 12 is inserted and seated properly in shaft 14. In this manner, a surgeon may have an audible confirmation that the shaft and tip are locked together.

In order to compel the tip 12 to be inserted in shaft 14 so that legs 24 and 26 align with access ports 38 and 40, alignment means 42 may be provided, generally consisting of tabs 44 and 46 extending saliently from shaft 14. Further, recesses 48 and 50 on tip 12 may also be provided. A handle or hub 60 is usually provided on the proximal end of shaft 14 and may be used to apply pressure to push the sharp end 16 of tip 12 through the body tissue. Shaft 14 is preferably hollow, at least at its distal end to provide for access ports 38 and 40 and permit the legs 24 and 26 of tip 12 to be inserted. To provide for strength, sharp cutting edges and the snap fitting action and sound, the trocar may be made of a metal or of a plastic such as of polycarbonate, ABS, polysulfone.

Figure 2:
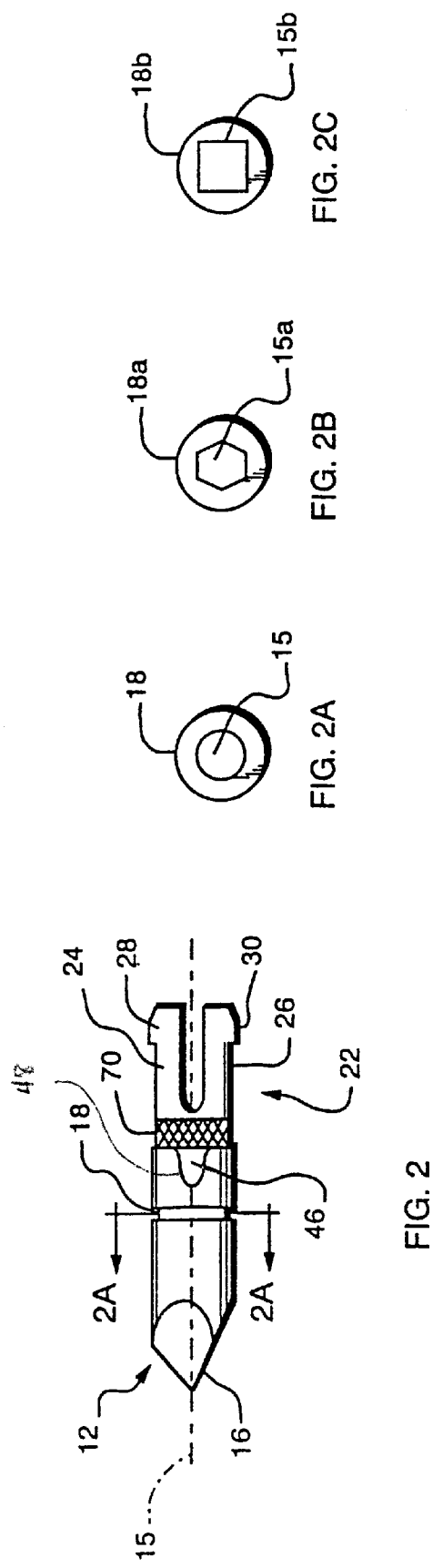
FIG. 2 is an enlarged detail view of the obturator tip of FIG. 1.

Visual indicia may be provided in the form of a contrasting color or texture or pattern 70, FIG. 2, which may be covered by cover portion 72, FIGS. 3 and 4, of shaft 14 when tip 12 is properly secured in shaft 14. In this manner, a surgeon may have another confirmation that the obturator is properly and safely assembled.

In operation, tip 12 is generally inserted in shaft 14 by simply pressing the ends of legs 24 and 26 against the cover portion 72 of shaft 14. Legs 24 and 26, being flexible, normally flex inward so that detents 28 and 30 may pass under the cover portion, preferably springing out in ports 38 and 40 (in some situations, making a clicking sound when detents 28 and 30 spring into position at stop recesses 34 and 36). At this point the color band 70 may no longer be visible as it is preferably hidden by the cover portion 72. When the surgical procedure is finished and it is desired to remove tip 12, tip 12 can be gripped by fingers or by a tool such as a forceps which may engage with groove 18 and then the surgeon may place a thumb and forefinger over access ports 38 and 40, depressing legs 24 and 26 so that detents 28 and 30 disengage from stop recesses 34 and 36.

Groove 18 may have a circular shape or circumference as shown in FIG. 2A, but it may as well have a polygonal shape such as hexagonal shape 18a, FIG. 2B, or square shape 18b, FIG. 2C, to better receive a wrench-like conformation or forceps.

Although in FIGS. 1–4, tip 12 is shown with a pair of flexible legs with detents and a pair of access ports as well as a pair of alignment tabs, these are not necessary limitations of the invention. As shown in FIG. 5, tip 12a may include a single recess 50a to receive a single salient tab 46a. Obturator tip 12a may have but a single flexible leg 24a with detent 28a; accessible through a single port 38a. All tabs 46 and recesses 50a used for alignment purposes may be eliminated, for example, and replaced by an alignment slot 80, FIG. 6, which may be asymmetrical and conformed to receive the asymmetrical shaped legs 24b and 78b so that the tip 12b can be automatically properly aligned with shaft 14b. Referring again to FIG. 5, element 78 which may take any particular form including a shape similar to leg 24a may be provided to keep tip 12a trued up and properly oriented in shaft 14a.

While the stop means thus far have been shown as a part of access ports 38 and 40, this is not a necessary limitation of the invention as they may in fact be constructed as internal stop shoulders 34c, 36c, FIG. 7, which may engage detents 28c and 30c on legs 24c and 26c.

Figure 9:
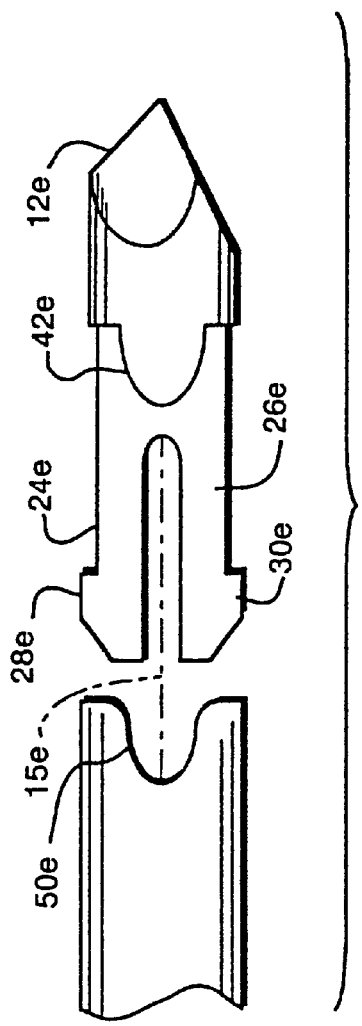
FIG. 9 is a view similar to FIG. 2 in which the alignment means have the salient portion on the tip and the mating recess portion on the shaft.

In addition, although thus far the flexible leg or legs and detents have been shown as a part of the tip and the access ports and stops means have been shown as a part of the shaft, this is not a necessary limitation of the invention as the converse is also contemplated by this invention as shown in FIG. 8, where tip 12d may include access ports 38d and 40d having stop recesses 34d and 36d while shaft 14d may contain flexible legs 24d and 26d having detents 28d and 30d. In addition, although the alignment means have been shown with the salient tab on the shaft and the recess on the tip, this is not a necessary limitation of the invention, for as shown in FIG. 9, one or more salient tabs 42e may be provided on tip 12e to self-center and nest in one or more recesses 50e.

Figure 10:
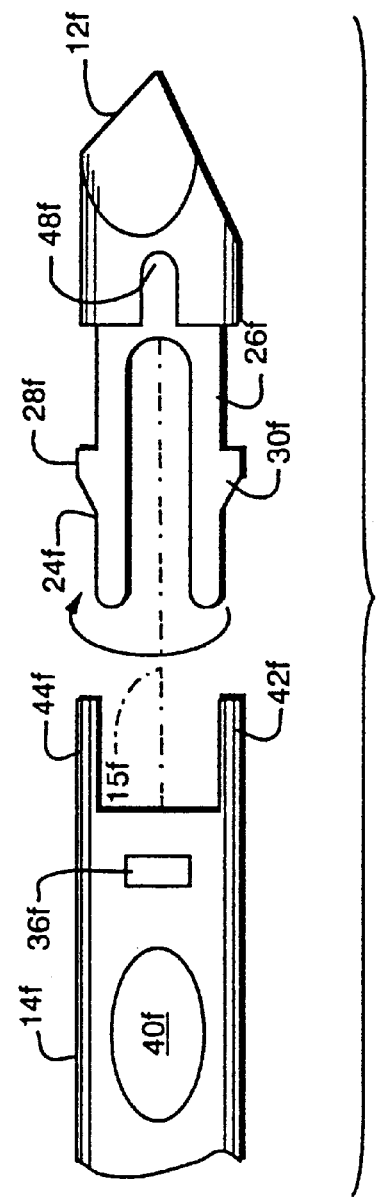
FIG. 10 is a view similar to FIG. 9 of another embodiment of the removable replaceable tip of this invention in which the stop means includes a stop recess separate from the access port.

The access port or ports for reaching flexible legs and compressing them inwardly against their bias may not provide a recessed stop as a part of its configuration. Rather, as show in FIG. 10, where tip 12f is shown as having been rotated 90 degrees with respect to shaft 14f, the stop recess 36f may be independently provided to engage detent 28f on leg 24f and a similar stop recess, not shown, may be provided on the opposite side of shaft 14f. Note that the assembly in FIG. 10 has been shown in an orientation to provide the best visualization of the specific embodiment shown, therefore, in FIG. 10, for proper rotational orientation of the tip 12f and shaft 14f, tip 12f must be rotated so that leg 24f comes out of the paper and leg 26f rotates into the paper about the central longitudinal axis 15f so that detent 24f fits into stop recess 36f.

Figure 11:
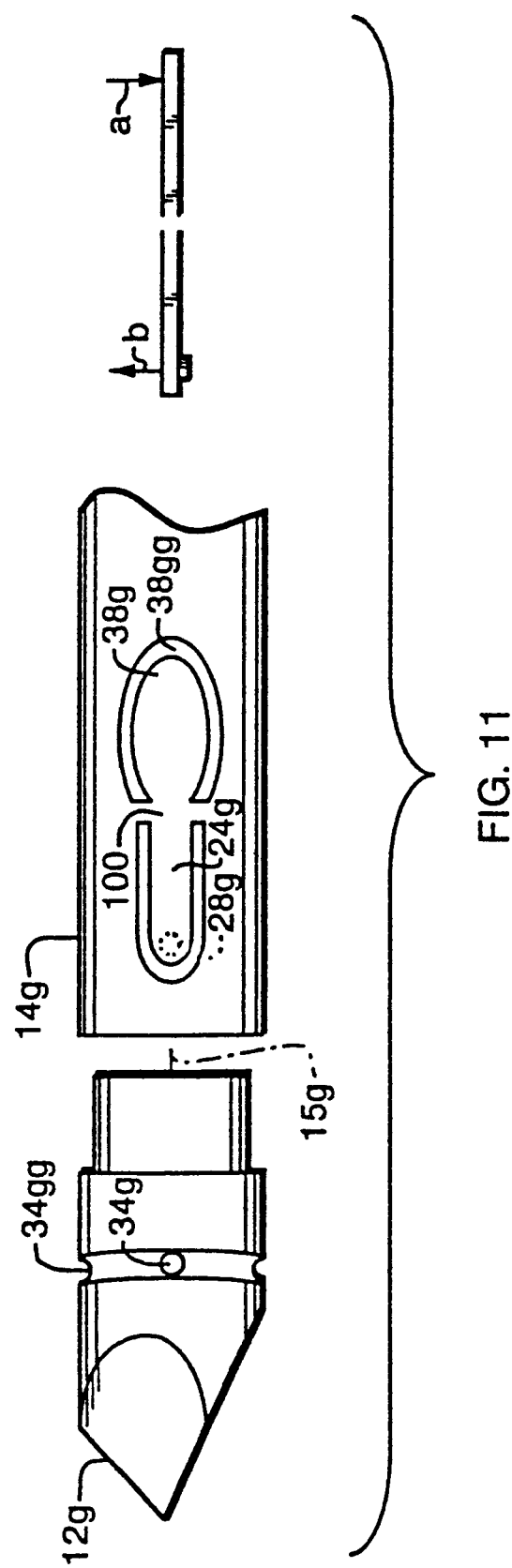
FIG. 11 is a view similar to FIG. 9 of another embodiment of the removable replaceable tip of this invention in which the detent is borne by a flexible leg interconnected with a resilient actuator tab on the shaft and the stop recess is a circumferential groove on the tip.

Although the access means has been shown as one or more ports, this is not a necessary limitation of the invention, For example, as shown in GIF 11, flexible leg 24g, having internally extending detent 28g, may be flexibly interconnected at junction 100, FIG. 11, with access actuator tab 38g in opening 38gg so that a downward pressure on tab 38g rocks leg 24g upwardly, lifting detent 28g out of stop recess hole 34g. A similar construction may be duplicated on the opposite side of tip 12g and shaft 14g. Hole 34g may be replaced by a circumferential slot 34gg so that orientation is not a problem as detent 28g and a complementary one on the other side of shaft 14g can engage anywhere along groove 34gg.

Figure 12A:
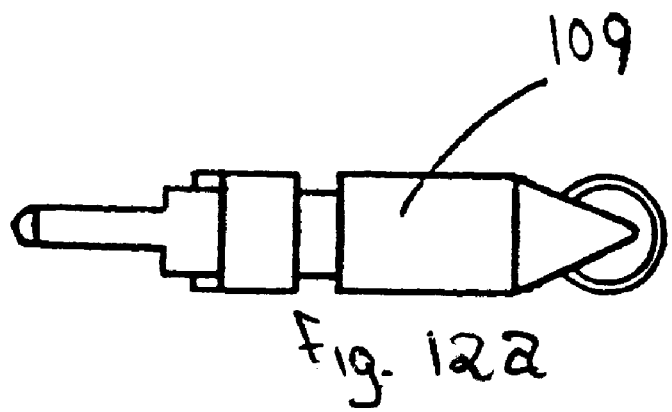
FIGS. 12a–p are top views of various obturator tips according to this invention.

FIGS. 12a–12p show an assortment of obturator tips that can be used on the obturator of this invention. The tips shown have a variety of cutting edges that may enable the surgeon to perform various intricate surgical procedures. Some of the cutting edges of the obturator tips shown in FIGS. 12a–12p include serrated cutting edges (i.e. FIGS. 12j and 12p, piercing cutting edges (i.e. FIGS. 12d and 12i, blunt cutting edges (i.e. FIG. 12o and radial cutting edges (i.e. FIGS. 12a, 12g and 12h).

Figure 12B:
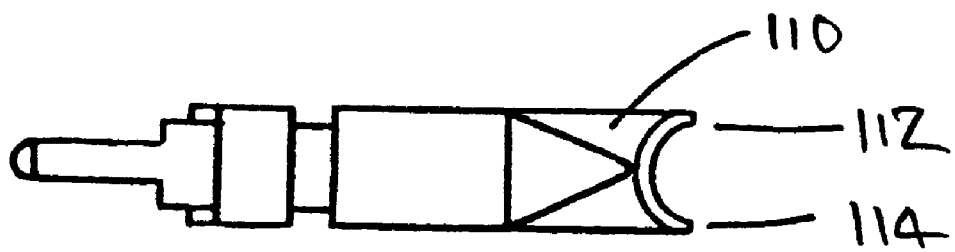
Figure 12C:
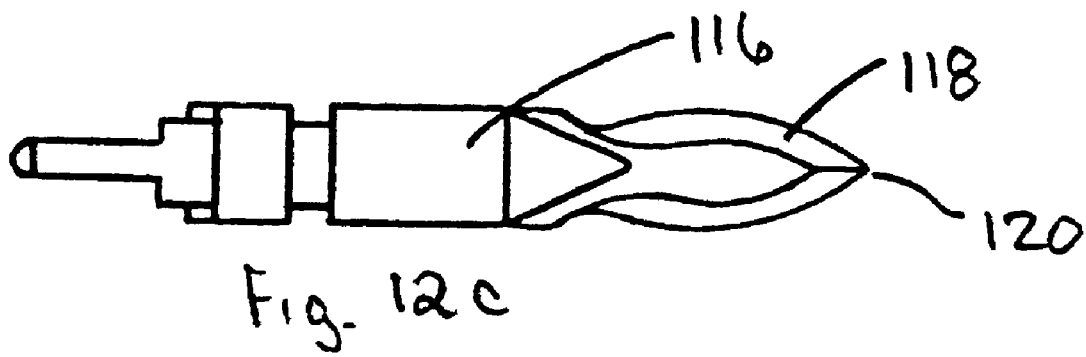
Figure 12D:
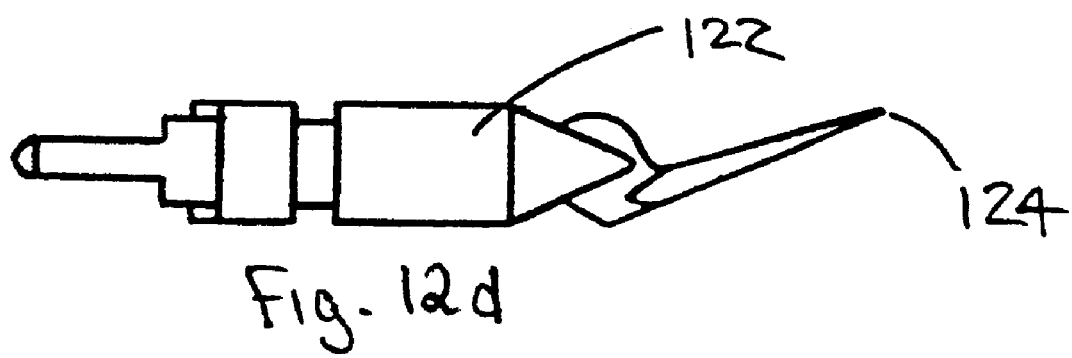

FIG. 12a shows a disc obturator tip 109 that preferably cuts and dilates in two directions and may provide an incision that is linear and easy to close. FIG. 12b shows a semi-circle obturator tip 110 which preferably cuts and dilates in two directions, provides a linear incision which is easy to close, and penetrates along two points 112 and 114. FIG. 12c shows a sword obturator tip 116 which may cut and dilate in two directions, may provide an incision which is linear and easy to close and may provide easy penetration with its double beveled 118 and pointed tip 120. FIG. 12d shows a claw obturator tip 122 which preferably cuts and dilates in two directions, provides an incision which is linear and easy to close, and may have a piercing tip 124 that generally allows for easy penetration. FIG. 12e shows a buck obturator tip with hook 126 that may cut and dilate in two directions, may provide an incision which is linear and easy to close and may allow for rotation of the surgeon's wrist and the obturator tip during entry. FIG. 12f shows a buck obturator tip 128 that generally cuts and dilates in two directions, provides a linear incision which is easy to close and allows for rotation of the surgeon's wrist and the tip during entry. FIG. 12g shows a swing obturator tip 130 which preferably cuts and dilates in two directions, provides a linear incision which is easy to close, and allows for rotation of the surgeon's wrist and the obturator tip during entry. FIG. 12h shows a 3/4 disc obturator tip 132 which generally cuts and dilates in two directions and may provide an incision which is linear and easy to close. FIG. 12i shows a triangular sword obturator tip 134 which may cut and dilate in two directions, may provide a linear incision which is easy to close, and generally allows for easy penetration with its double beveled 136 and pointed tip 138. FIG. 12j shows a 45 degree serrated obturator tip 140 which preferably cuts and dilates in two directions, provides a linear incision which is easy to close, and its point 142 and serration 144 preferably allow for ease of penetration for maximum cutting. FIG. 12k shows a "V" bevel obturator tip 146 which normally cuts and dilates in two directions, provides a linear incision which is easy to close and allows penetration force to be applied at two points 148 and 150. FIG. 12l is an extended buck obturator tip 152 which generally cuts and dilates in two directions, provides a linear incision which is easy to close and allows for rotation of the surgeon's wrist and the obturator tip during entry. FIG. 12m shows a hooked blade obturator tip with serration 154 which may cut and dilate in two directions, may provide a linear incision which is easy to close and may allow for pointed insertion and rotation during entry. FIG. 12n shows a sickle obturator tip 156 which generally cuts and dilates in two directions, provides a linear incision which is easy to close and allows for pointed insertion and rotation during entry. FIG. 12o shows a flat obturator tip 158 that may cut and dilate in two directions, may provide a linear incision that is easy to close, and may allow for direct entry with no rotation. FIG. 12p shows a sickle obturator tip with reverse rotation 160 which preferably cuts and dilates in two directions, provides a linear incision which is easy to close and allows for pointed insertion and rotation during entry.

Although specific features of this invention are shown in some drawings and not others, this is for convenience only as each feature may be combined with any or all of the other features in accordance with the invention.

Other embodiments will occur to those skilled in the art and are within the following claims:

1. An obturator assembly comprising:
   a removable obturator tip having a sharpened distal end and a proximal end;
   a first engagement device disposed on the proximal end of the removable obturator tip; an obturator shaft having a distal end;
   a second engagement device disposed on the distal end of the obturator shaft adapted to lockingly engage the first engagement device, thereby securing the removable obturator tip to the obturator shaft; and
   a biased flexible member which functions: (a) to flexibly engage the first engagement device to the second engagement device, the flexible member being accessible, when said first and second engagement devices are engaged; and (b) to disengage the first engagement device from the second engagement device by flexing the flexible member against its bias.

2. The obturator assembly of claim 1, wherein the sharpened distal end of the obturator tip has a serrated cutting edge.

3. The obturator assembly of claim 1, wherein the sharpened distal end of the obturator tip has a piercing cutting edge.

4. The obturator assembly of claim 1, wherein the sharpened distal end of the obturator tip has a blunt cutting edge.

5. The obturator assembly of claim 1, wherein the sharpened distal end of the obturator tip has a radial cutting edge.

6. The obturator assembly of claim 1, wherein the sharpened distal end of the obturator tip has a cutting edge that cuts and dilates in two directions.

7. The obturator assembly of claim 1, wherein the sharpened distal end of the obturator tip makes an incision that is linear and easy to close.

8. The obturator assembly of claim 1, wherein the sharpened distal end of the obturator tip has a semi-circular cutting edge.

9. The obturator assembly of claim 1, wherein the sharpened distal end of the obturator tip penetrates at two points.

10. The obturator assembly of claim 1, wherein the sharpened distal end of the obturator tip has a double beveled cutting edge.

11. The obturator assembly of claim 1, wherein the sharpened distal end of the obturator tip has a claw shaped cutting edge.

12. The obturator assembly of claim 1, wherein the sharpened distal end of the obturator tip creates an incision that allows the obturator tip to be rotated as the incision is made.

13. The obturator assembly of claim 1, wherein the sharpened distal end of the obturator tip has a triangular cutting edge.

14. The obturator assembly of claim 1, wherein the sharpened distal end of the obturator tip has a hooked blade cutting edge.

15. The obturator assembly of claim 1, wherein the sharpened distal end of the obturator tip has a sickle shaped cutting edge.

16. The obturator assembly of claim 1, wherein the sharpened distal end of the obturator tip has a flat cutting edge.

17. An obturator assembly comprising:
    a removable obturator tip having a sharpened distal end and a proximal end;
    a biased flexible leg extending from the proximal end of the tip, the flexible leg having a detent;
    an obturator shaft having a stop for engaging the detent on the biased flexible leg to connect the tip to the obturator shaft; and
    an access port formed in the obturator shaft to permit movement of the flexible leg against its bias to disengage the detent from the stop.

18. The obturator assembly of claim 17, wherein the sharpened distal end of the obturator tip has a serrated cutting edge.

19. The obturator assembly of claim 17, wherein the sharpened distal end of the obturator tip has a piercing cutting edge.

20. The obturator assembly of claim 17, wherein the sharpened distal end of the obturator tip has a blunt cutting edge.

21. The obturator assembly of claim 17, wherein the sharpened distal end of the obturator tip has a radial cutting edge.

22. The obturator assembly of claim 17, wherein the sharpened distal end of the obturator tip has a cutting edge that cuts and dilates in two directions.

23. The obturator assembly of claim 17, wherein the sharpened distal end of the obturator tip makes an incision that is linear and easy to close.

24. The obturator assembly of claim 17, wherein the sharpened distal end of the obturator tip has a semi-circular cutting edge.

25. The obturator assembly of claim 17, wherein the sharpened distal end of the obturator tip penetrates at two points.

26. The obturator assembly of claim 17, wherein the sharpened distal end of the obturator tip has a double beveled cutting edge.

27. The obturator assembly of claim 17, wherein the sharpened distal end of the obturator tip has a claw shaped cutting edge.

28. The obturator assembly of claim 17, wherein the sharpened distal end of the obturator tip creates an incision that allows the obturator tip to be rotated as the incision is made.

29. The obturator assembly of claim 17, wherein the sharpened distal end of the obturator tip has a triangular cutting edge.

30. The obturator assembly of claim 17, wherein the sharpened distal end of the obturator tip has a hooked blade cutting edge.

31. The obturator assembly of claim 17, wherein the sharpened distal end of the obturator tip has a sickle shaped cutting edge.

32. The obturator assembly of claim 17, wherein the sharpened distal end of the obturator tip has a flat cutting edge.

* * * * *